United States Patent [19]

Kipke

[11] Patent Number: 5,702,250
[45] Date of Patent: Dec. 30, 1997

[54] COMPACT DENTAL IMPRESSION TRAY FOR PHOTOCURABLE IMPRESSION MATERIAL

[75] Inventor: Cary A. Kipke, Woodbury, Minn.

[73] Assignee: Minnesota Mining and Manufacturing Co., St Paul, Minn.

[21] Appl. No.: 684,522

[22] Filed: Jul. 19, 1996

[51] Int. Cl.$^6$ .............................. A61C 1/00; A61C 3/00
[52] U.S. Cl. ........................................ 433/37; 433/29
[58] Field of Search ........................ 433/29, 37, 215, 433/214, 229; D26/2, 3, 27; 362/806, 811, 362

[56] References Cited

U.S. PATENT DOCUMENTS

| 1,084,017 | 1/1914 | Lautenburg . | |
|---|---|---|---|
| 4,449,928 | 5/1984 | von Weissenfluh | 433/40 |
| 4,553,936 | 11/1985 | Wang | 433/37 |
| 4,666,406 | 5/1987 | Kanca, III | 433/229 |
| 4,761,136 | 8/1988 | Madhavan et al. | 433/214 |
| 4,790,752 | 12/1988 | Cheslak | 433/37 |
| 4,802,851 | 2/1989 | Rhoades | 433/93 |
| 4,818,231 | 4/1989 | Steiner et al. | 433/215 |
| 4,867,680 | 9/1989 | Hare et al. | 433/37 |
| 4,867,682 | 9/1989 | Hammesfahr et al. | 433/37 |
| 4,888,489 | 12/1989 | Bryan | 250/504 H |
| 5,030,093 | 7/1991 | Mitnick | 433/164 |
| 5,145,886 | 9/1992 | Oxman et al. | 522/66 |
| 5,179,186 | 1/1993 | Müller et al. | 528/49 |
| 5,316,473 | 5/1994 | Hare | 433/29 |
| 5,487,662 | 1/1996 | Kipke et al. | 433/37 |

FOREIGN PATENT DOCUMENTS

| 0 273 085 | 3/1986 | European Pat. Off. . |
| 0 170 219 | 8/1987 | European Pat. Off. . |
| 0 255 286 | 2/1988 | European Pat. Off. . |
| 0 269 071 | 6/1988 | European Pat. Off. . |
| 0 460 478 | 12/1991 | European Pat. Off. . |
| WO 95/07731 | 3/1995 | WIPO . |

OTHER PUBLICATIONS

Genesis™ brochure, Dentsply International, Inc., copyright 1988.

Primary Examiner—Nicholas D. Lucchesi
Attorney, Agent, or Firm—Gary L. Griswold; Walter N. Kirn; James D. Christoff

[57] ABSTRACT

A dental impression tray includes at least one array of solid state light emitters for curing photocurable impression material received in a channel of the tray. The tray includes a body presenting the channel, and a housing that is detachably connected to the body. The tray preferably includes a battery that extends along a buccolabial side of the tray body and as a result is received in the patient's oral cavity when an impression is taken.

27 Claims, 3 Drawing Sheets

COMPACT DENTAL IMPRESSION TRAY FOR PHOTOCURABLE IMPRESSION MATERIAL

BACKGROUND OF THE INVENTION

1. Field of the Invention

This invention broadly relates to a dental impression tray that is adapted for use with impression materials that cure upon exposure to light.

2. Description of the Related Art

Dental impression trays are used to hold impression material for making a model of a patient's tooth and oral tissue anatomy so that a crown, bridge, denture, veneer, restoration or the like can be made. A typical procedure involves placing a quantity of impression material in an open trough or channel of the tray and then pressing the tray onto the dental arch of the patient. The impression material is allowed to cure while in the oral cavity. The tray with the impression material is then removed from the oral cavity, and the impression material is used to prepare a positive model that replicates the selected area of the patient's arch.

Most conventional dental impression materials are made by mixing two components immediately before the impression is taken. Mixing of the components initiates a polymerization reaction that eventually causes the material to harden and cure. Consequently, as soon as the components are mixed, it is important for the dental practitioner to promptly deliver the tray to the oral cavity and accurately position the impression material relative to the selected area of the dental arch so that an accurate impression can be made.

Typically, a manufacturer of dental impression material provides recommended guidelines to the practitioner that specify both a working time and a setting point time to be followed when using the material. The working time is determined by the composition of the polymeric system and is the total time allowed for mixing the components, placing the mixed components in the tray, delivering the tray to the oral cavity and accurately seating the impression material onto desired areas of the patient's dental arch. The setting point time relates to the degree of curing of the impression material, and represents the total time that should elapse (after the components are mixed) before the tray is removed from the oral cavity in order to ensure that the impression material has cured to a degree sufficient that the impression will not be distorted as the tray is removed from contact with the dental arch.

A variety of dental impression materials are currently available that polymerize upon mixing of two components. Such materials include, for example, hydrocolloids, polysulfides, polyethers and silicones. Recommended working times and setting point times for such materials are often in the range of about 1.25 to 7 minutes and 1.5 to 10 minutes respectively.

Unfortunately, dental impression materials that begin to polymerize upon mixing are not entirely satisfactory, in that taking of the impression should be completed within a predetermined amount of time. If, for example, the procedure is interrupted by the dentist or by the patient for some unforeseen reason, the impression material may cure to such a degree that it is unusable before the procedure can be resumed. Another problem associated with such impression materials relates to the differences in recommended working times and setting point times for the variety of materials that are currently available, since a dental practitioner who has long used one type of material may fail to follow the manufacturer's recommended working time and setting point time for another material that is substituted.

In many impression materials that cure upon mixing, the length of the working time and the setting point time are determined by the amount of catalyst in the mixture. As a consequence, one who attempts to decrease the setting point time by increasing the catalyst concentration may be frustrated because the working time may also be unduly shortened. Conversely, an attempt to increase the working time may result in lengthening the setting point time by an unsatisfactory amount.

It has been suggested that the use of photopolymerizable dental impression materials overcomes the disadvantages often associated with impression materials that are curable when mixed. Photopolymerizable impression materials include a photocatalyst and/or a photoinitiator that initiates polymerization of the impression material upon exposure to an appropriate o wavelength of light. In the absence of such a light source, the impression material will remain substantially unpolymerized for a relatively long period of time so that the dental practitioner can ensure that the tray is accurately positioned before the impression material cures. Examples of photocurable materials are set out in U.S. Pat. Nos. 5,179,186, 5,145,886, 4,761,136, 4,543,063 and 4,740, 159 and European patent applications publication nos. 0460478, 0269071, 0255286, 0173085 and 0170219.

Photopolymerizable impression materials also provide a potential advantage in instances where the tray is accurately placed in the mouth in a relatively short amount of time. In such instances, the light source can be immediately activated to begin curing of the impression material, so that the overall time necessary to complete the impressioning procedure can be reduced. By contrast, a practitioner using an impression material that immediately begins to cure upon mixing is generally unable to shorten the time necessary for completion of the impressioning procedure even when the tray is quickly placed in the oral cavity because polymerization reaction will proceed at the same rate.

An improved dental impression tray that is especially adapted for use with photocurable dental impression material is described in U.S. Pat. No. 5,487,662 and includes a body having a channel, and at least one solid state emitter mounted on the body for curing dental impression material in the channel. The solid state emitters provide an efficient source of light that can be located closely to the dental impression material in the channel, and yet are relatively small so that proper placement of the tray in the oral cavity is not hindered. Preferably, each solid state emitter emits light having a wavelength in the range of about 630 to 980 nanometers in order to better penetrate the soft oral tissue and enhance curing of the impression material in gingival and sub-gingival regions in comparison to light having wavelengths near the center of the visible spectrum.

The dental impression tray described in U.S. Pat. No. 5,487,662 optionally includes at least one light detector to monitor light flux in the channel, and a controller to vary current to each emitter in response to changes of the light flux sensed by the detector. The light detector preferably senses changes in reflective optical properties of the dental impression material as the latter cures, and optionally activates an alarm in response to one or more certain changes in the sensed optical reflective properties to signal that polymerization is substantially complete.

The solid state light emitters that provide light for the dental impression tray described in U.S. Pat. No. 5,487,662 receive power from a battery pack that is connected to the tray, or by a power supply such as a filtered, rectified power supply adapted to be placed on a countertop near the patient's chair. In the specific embodiments shown in the drawings of U.S. Pat. No. 5,487,662, a battery pack is detachably connected to a body of the tray that contains the channel for receiving the impression material, and the battery pack is located outside of the oral cavity when an impression of a patient's dental arch is taken.

While the dental impression tray described in U.S. Pat. No. 5,487,662, represents a significant advance in the art, there is a continuing need to improve dental impression trays in order to facilitate use of the tray and taking of the impression in a manner that is convenient for the dental practitioner. Furthermore, there is a continuing need in the art to improve dental impression trays in such a manner that the accuracy and detail of the resultant impression is enhanced.

SUMMARY OF THE INVENTION

The present invention is directed in one aspect toward a dental impression tray that comprises a body having a channel for receiving a quantity of photocurable dental impression material, wherein the body has a lingual side and a buccolabial side. The tray also comprises at least one solid state light emitter that is coupled to the body for directing light into the channel. At least one battery is electrically connected to the emitter(s) and is coupled to the body. The at least one battery extends along at least one of the lingual side and the buccolabial side of the body.

The present invention is also directed toward a dental impression tray that comprises a body having a channel for receiving a quantity of photocurable dental impression material, wherein the body has a lingual side and a buccolabial side. A housing is detachably connected to the body and extends along the lingual side and the buccolabial side of the body. At least two arrays of solid state emitters are connected to the housing and include at least two distinct, flat emitter-supporting substrates. At least one of the substrates extends along the lingual side of the body, and at least one of the substrates extends along the buccolabial side of the body.

Another aspect of the present invention is directed toward a dental impression tray that comprises a body having an elongated channel for receiving a quantity of photocurable dental impression material, wherein the body has a lingual side and a buccolabial side. The tray also comprises a housing that is detachably connected to at least one of the sides of the body. At least one solid state light emitter is connected to the housing for directing light into the channel. The housing is detachable from the body by sliding the housing relative to the body in directions along the longitudinal axis of the channel.

The dental impression tray of the present invention in its various embodiments is relatively compact and therefore can be readily maneuvered within the oral cavity to a selected position as needed. Such construction also enables the center of gravity of the tray to be closely adjacent the selected area of the oral cavity where the impression is taken and also enables the overall weight of the tray to be reduced in comparison to prior impression trays. As a result, the present invention increases the likelihood of taking an accurate, detailed impression without undue distortion of the impression material as the impression material cures.

These and other features of the invention are described in more detail below and in the accompanying drawings.

DETAILED DESCRIPTION OF THE PREFERRED EMBODIMENTS

Figure 1:
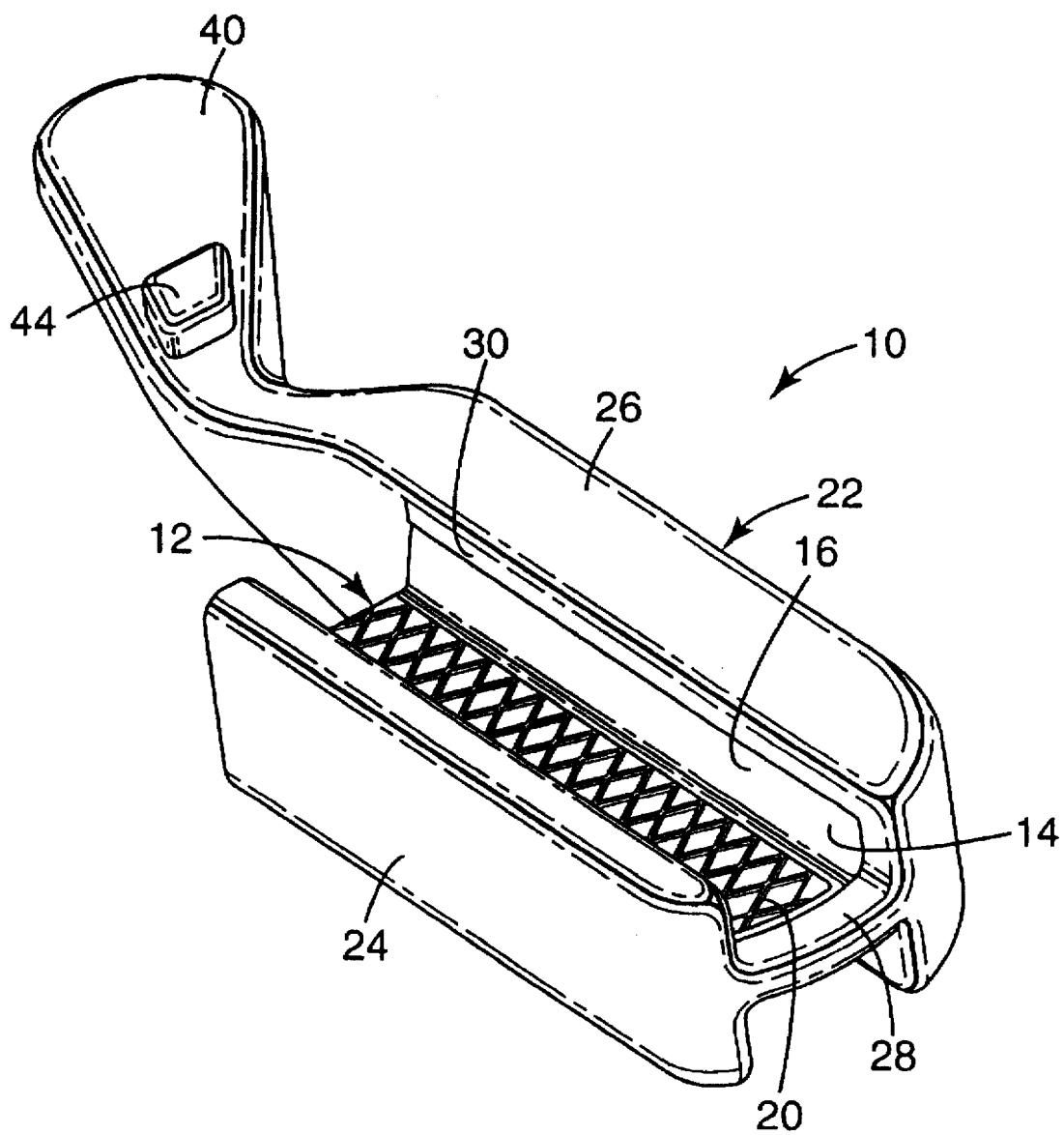
FIG. 1 is a perspective view of a dental impression tray constructed in accordance with one embodiment of the present invention.
Figure 2:
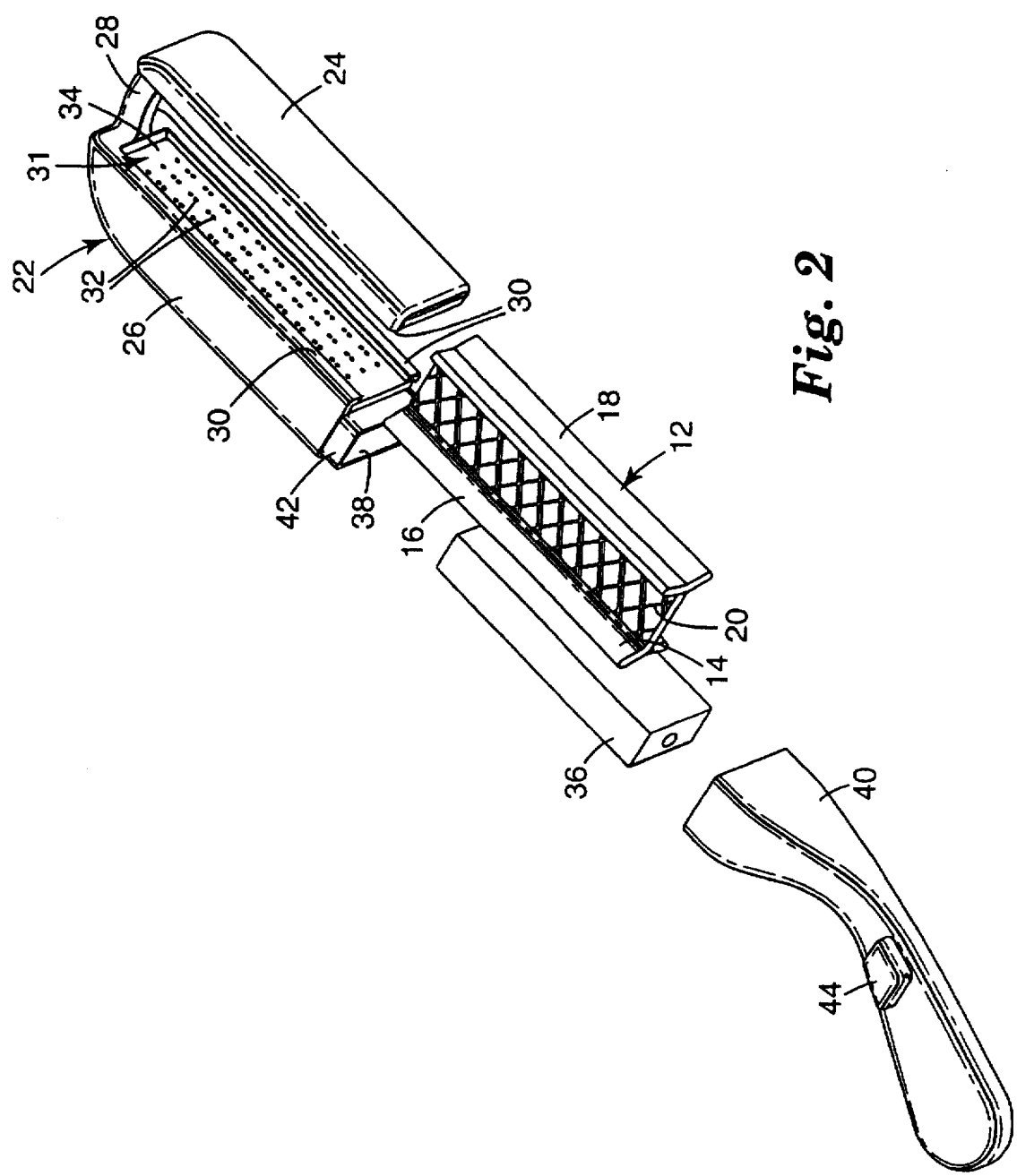
FIG. 2 is a perspective view of the tray shown in FIG. 1 when viewing the tray from a different orientation, and showing the tray partially disassembled.

A dental impression tray according to one embodiment of the invention is designated broadly by the numeral 10 in FIGS. 1 and 2. The tray includes a body 12 having an elongated channel 14 for receiving a quantity of photocurable dental impression material.

The body 12 has a generally "H"-shaped configuration, and the channel 14 includes an upper channel section and a lower channel section. Each of the channel sections is adapted to receive photocurable dental impression material in order to simultaneously take an impression of a portion of both the patient's upper and lower dental arch.

The body 12 may have other configurations as well. For example, the channel 14 may have only a single channel section and have a "U"-shaped configuration in directions transverse to its longitudinal axis in order to take an impression of only one of the patient's dental arches. As other options, the body 12 may have a "J"-shaped configuration or a "U"-shaped configuration in plan view that is adapted to match half or all of one or both of the patient's dental arches. Such "J"-shaped or "U"-shaped bodies could have a single channel section for taking an impression of all or a portion of only one dental arch, or two channel sections for taking an impression of all or a portion of both dental arches.

The body 12 that is illustrated in FIGS. 1 and 2 includes a buccolabial side 16 (i.e., a side that is located between the dental arch and the lips or cheeks of the patient) and a lingual side 18 (i.e., a side that is located between the dental arch and the patient's tongue). A septurn 20 integrally interconnects the buccolabial side 16 and the lingual side 18. The septurn 20 separates the upper channel section from the lower channel section and is optionally provided with a series of apertures. In the embodiment shown in FIGS. 1 and 2, the septurn 20 is a mesh made of interwoven fibers arranged in a diagonal pattern. Optionally, the fibers are optical fibers that facilitate distribution of light from the sides 16, 18 of the body 12 to various regions of the upper channel section and the lower channel section.

The tray 10 also includes an elongated housing 22 that is detachably connected to the body 12. The housing 22 includes a lingual section 24, a buccolabial section 26 and a distal section 28 that interconnects the lingual section 24 and the buccolabial section 26. The lingual section 24 extends in a direction along the lingual side 18 of the body 12, while the buccolabial section 26 extends in a direction along the buccolabial side 16 of the body 12.

Both of the housing sections 24, 26 include a pair of opposed flanges 30 that extend in directions along the longitudinal axis of the housing 22. Each of the flanges 30 forms a channel that receives a respective edge portion of one of the sides 16, 18 of the body 12.

The flanges 30 and the edge portions of the buccolabial and lingual sides 16, 18 form a tongue and groove arrangement that serves to detachably connect the body 12 to the housing 22. The body 12 can be removed from the housing 22 by sliding the body 12 away from the distal housing section 28 in a direction along the longitudinal axis of the channel 14 (which is parallel to the longitudinal axis of the housing 22) until the sides 16, 18 are free from engagement with the flanges 30. The body 12 can be reconnected to the housing 22 when desired by moving the edge portions of the sides 16, 18 into the channels defined by the flanges 30 and then sliding the body 12 toward the distal housing section 28 in a direction along the longitudinal axis of the channel 14.

The tray 10 also includes two arrays 31 of solid state light emitters 32. One of the arrays 31 is carried by the lingual section 24 of the housing 22, and the other array 31 is carried by the buccolabial section 26 of the housing 22. Each of the arrays 31 includes a flat, rectangular substrate 34 that provides a mounting panel for the respective light emitters 32.

As used herein, the phrase "solid state light emitter" means any device that converts electric energy into electromagnetic radiation through the recombination of holes and electrons. Examples of solid state light emitters include semi-conductor light emitting diodes, semi-conductor laser diodes, polymer light emitting diodes and electroluminescent devices (i.e., devices that convert electric energy to light by a solid phosphor subjected to an alternating electric field). The light preferably has wavelengths in the visible range (i.e., from about 400 nanometers to about 700 nanometers), in the near-infrared range (i.e., such as from about 700 nanometers to about 980 nanometers), or both. A particularly preferred wavelength range is known as the therapeutic window for tissue transmission and extends from about 630 nanometers to about 980 nanometers. The wavelength of the emitted radiation is selected to provide optimum photoinitiation of dental impression material received in the channel 14, and accordingly is selected by reference to the type of photoinitiator employed in the impression material.

Suitable light emitting diodes are p-n junction heterostructures made from semiconductor materials that are doped to result in the emission of light within a desired, preferably narrow, band of wavelengths that match the wavelength band of light that is absorbed by the photoinitiator or photocatalyst. Such heterostructures are also referred to as "optical devices" or "chips". Suitable semiconductor materials include AlGaAs for providing light in a selected wavelength band that lies in the range of about 600 to 900 nanometers, InGaAs for providing light in a selected wavelength band that lies in the range of about 900 to 980 nanometers, and AlGaInP for providing light in a selected wavelength band that lies in the range of about 560 to 650 nanometers. The selected wavelength band is determined by the choice of doping level in the fabrication of the semiconductor chip.

Light emitting diode assemblies that include semiconductor chips providing light in the above-mentioned visible or near-infrared ranges are commonly sold, but are typically assembled or packaged with a relatively bulky focusing lens and a pair of wire leads. Examples of such assemblies include nos. E21, E22, E100, E102, E104 and E106 from Gilway Technical Lamp of Woburn, Mass. Preferably, however, the emitters 32 lack such lenses and leads and include only the relatively small semiconductor chips so that the overall size of the tray 10 is relatively compact and the light is emitted in many directions.

The use of light emitting diodes as emitters 32 is particularly advantageous in that the diodes provide light having selected wavelengths in a relatively narrow range that optimizes initiation of the polymerization reaction. Moreover, if the selected diode emits light having wavelengths in the therapeutic window, the intensity of the light is greater than the intensity that would be provided by similar light emitting diodes operating near the center of the visible wavelength region. Light having wavelengths in the therapeutic window provides better penetration of the soft oral tissue and may provide improved curing of the impression material in gingival and sub-gingival regions in comparison to light having wavelengths near the center of the visible spectrum. Such light also penetrates the impression material more deeply because the light is scattered less than light having shorter wavelengths.

Preferably, the substrate 34 is a flat printed circuit board having conductive buses that are arranged in a predetermined pattern for proper placement of the emitters 32 in the array 31. For example, the bottom of each emitter 32 may have an N-type terminal in electrical contact with one conductive bus, and a top, P-type terminal of each emitter 32 may be connected by a small wire bond to a second conductive bus. The emitters 32 are preferably mounted on the substrate 34 in an automated manufacturing process using robotics.

The arrays 31 including the emitters 32, the conductive buses and the wire bonds are preferably covered with an electrically non-conductive transparent or translucent protective polymeric coating that extends along the entire side of the substrate 34 facing the body 12. Suitable materials for the coating include clear epoxies. The coating may have either a smooth or textured surface.

The tray 10 also includes a battery 36 that is carried by the housing 22. Preferably, the battery 36 extends along one of the sides 16, 18 of the body 12, and more preferably extends along only the buccolabial side 16 of the body 12. Alternatively, however, the battery 36 could extend along only the lingual side 18, or one or more batteries could extend along each of the sides 16, 18.

Preferably, the battery 36 is received in a chamber 38 of the housing 22 and is completely enclosed in the housing 22. The battery 36 that is shown in FIG. 2 has a rectangular configuration, although other battery configurations are also possible. For example, a round battery or a series of round batteries may be preferred in some instances to better withstand a sterilization procedure for the tray 10, such as an autoclaving process using steam. Optionally, the battery 36 is rechargeable.

The housing 22 also includes a handle section 40 that is releasably coupled to the buccolabial section 26. As illustrated in FIG. 2, the buccolabial section 26 includes a protruding, rectangular coupling flange 42 that fits within a mating cavity of the handle section 40. The flange 42 presents a slight interference fit with the cavity of the handle section 40 in order to securely retain the handle section 40 in coupled relationship with the buccolabial section 26 by means of friction.

The handle section 40 includes a pair of electrical contacts. One of the contacts is located at the mesial end of the cavity of the handle section 40 and engages the round battery terminal that is shown in FIG. 2 when the handle section 40 is connected to the buccolabial housing section 26. The other contact is located on one of the sides of the cavity of the handle section 40 and engages a mating contact that is positioned on one side of the protruding flange of the buccolabial section 26 when the handle section 40 is connected to the buccolabial section 26.

A push button switch 44 is mounted on the handle section 40 for energization of the light emitters 32 when desired. Preferably, the switch 44 is a sealed, momentary-type membrane switch without protruding parts that might otherwise hinder sterilization.

The body 12 also includes leads for electrically connecting together the switch 44, the battery 36, the emitters 32 and the various electrical contacts. Although not illustrated in the drawings, the leads are connected to the conductive buses on the substrates 34, and include portions that extend through a passageway in the distal section 28 in order to electrically connect the two light emitter arrays 31 together. The distal end of the chamber 38 includes an electrical contact connected to one of the leads and position to engage a terminal on the distal end of the battery 36.

Optionally, the handle section 40 contains a microcontroller to enhance operation of the tray 10. For example, the microcontroller could include circuitry that provides a pulsed current to the light emitters 32 in order to increase the temporal photon flux. The microcontroller may also include a timing circuit to activate the light emitters 32 for a predetermined amount of time once the switch 44 is depressed.

As another option, the microcontroller may be connected to light detectors that are mounted on one or both of the substrates 34. The light detectors monitor light flux within the channel 14. The microcontroller turns the various emitters 32 on or off as needed in various regions of the channel 14, or alternatively varies the current level of various emitters 32 to obtain a desired light flux. As another alternative, the light detectors monitor the curing of the impression material by detecting changes in reflectance optical properties of the impression material. The reflectance changes can be the result of changes in light scattering by the polymerized material and/or by optical absorption by the photocatalyst or photoinitiator. The detectors and the microcontroller may be used to alter or interrupt current to some or all of the light emitters 32, and/or to activate an audible alarm that signals that polymerization is complete.

The handle section 40 preferably is connected to the buccolabial section 26 during autoclaving so that the contacts of the battery 36 and the terminals within the chamber 38 of the housing 22 remain covered. Preferably, the flange 42 provides a seal for the chamber 38 of the housing 22 when the handle section 40 is assembled to the buccolabial section 26 in order to enable the battery 36 and the contacts and terminals to resist any adverse affects caused by sterilization procedures. However, the handle section 40 may be disconnected from the buccolabial section 26 when desired in order to provide access to the battery 36 as may be needed, for example, when the battery 36 is to be recharged or replaced.

Advantageously, the orientation of the battery 36 alongside the buccolabial section 26 of the housing 22 provides a convenient, compact construction, since the battery 36 is located completely within the oral cavity when the impression is taken. As a result, the mass of the battery 36 is closely adjacent the patient's tooth structure, and is not located outside of the oral cavity as with previously known impression trays. Such construction helps ensure that the center of gravity of the tray 10 is close to the patient's dental arches and reduces the likelihood of adverse effects due to any moment arms caused by the weight of the battery 36. As a consequence, the resulting impression is likely to be relatively free of distortions that might otherwise be caused by movement of the tray when the impression is taken.

Figure 3:
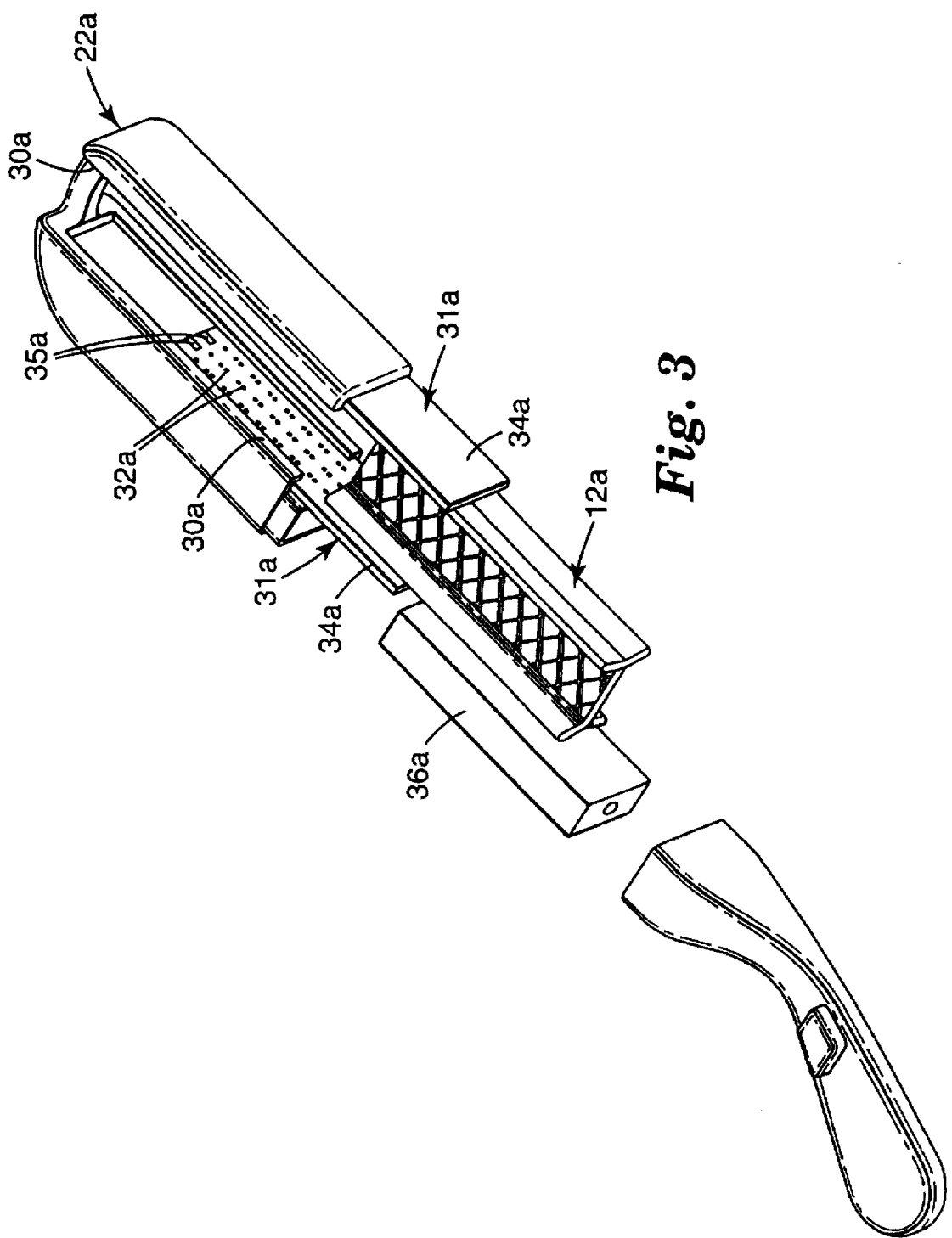
FIG. 3 is a perspective view of a dental impression tray constructed in accordance with another embodiment of the invention, wherein the tray is shown partially disassembled.

Another embodiment of the present invention is illustrated in FIG. 3, wherein a dental impression tray 10a includes a body 12a and a housing 22a that is detachably connected to the body 12a. The tray 10a also includes a battery 36a that is received in a chamber of the housing 22a. The body 12a, the housing 22a and the battery 36a are identical to the body 12, the housing 22 and the battery 36 respectively described above with the exceptions as noted below, and as such a detailed description of such items need not be repeated.

The tray 10a also includes two arrays 31a of solid state light emitters 32a that are mounted on a respective one of two rectangular substrates 34a. The emitters 32 are identical to the light emitters 32 described above. The substrates 34a are identical to the substrates 34 described above, except that the distal end of each substrate 34a includes a series of contact terminals 35a.

Each of the arrays 31a is detachably connected to the body 12a. The arrays 31a are slidably received in a channel established by flanges 30a located on the housing 22a. The flanges 30a also slidably receive the body 12a and are somewhat wider than the flanges 30.

The arrays 31a are connected to the housing 22a by sliding each array 31a in a longitudinal direction toward a distal section of the housing 22a. As the arrays 31a slide into a fully received position in the housing 22a, the terminals 35a engage mating terminal receptacles (not shown) mounted near the distal section of the housing 22a in order to electrically connect the light emitters 32a to other circuitry of the tray 10a including the battery 36a.

The removable light emitter arrays 31a of the tray 10a are an advantage in that the arrays 31a can be easily replaced when desired. Moreover, in some constructions it may be desirable to avoid exposure of the light emitter arrays 31a to autoclaving. In such instances the light emitter arrays 31a are removed from the housing 22a before the latter is placed in the autoclave.

The tray bodies 12, 12a, being detachable from the tray housings 22, 22a, are an advantage in that a number of relatively inexpensive tray bodies 12, 12a may be retained on hand, while only a small number of the relatively expensive housings 22, 22a need be purchased. Such construction is a particular advantage in instances where the dental practitioner desires to send the body 12, 12a and the resultant impression to an outside laboratory for making a model or statue of the selected tooth structure. Moreover, such construction is an advantage in instances where the tray 10, 10a is used to take more than one impression on a single patient, since the housing 22, 22a need not be resterilized when a second body 12, 12a is connected to the housing 22, 22a for a second impression.

The tray bodies 12, 12a are preferably integrally made of a clear plastic material such as polycarbonate. The tray housings 22, 22a are made of any suitable plastic material that preferably can withstand autoclaving, such as polycarbonate.

Those skilled in the art will recognize that a number of variations and additions to the presently preferred embodiments described above may be effected without departing from the spirit of the invention. For example, the light emitter arrays may be received in corresponding chambers of the tray housing in enclosed fashion. As another alternative, the substrates of the light emitters may be made of a flexible material and curved or bent as needed to match the configuration of sides of the tray. As such, the invention should not be deemed limited to the embodiments described above in detail, but only by a fair scope of the claims that follow along with their equivalents.

I claim:

1. A dental impression tray comprising:
   a body having a channel for receiving a quantity of photocurable dental impression material, said body having a lingual side and a buccolabial side;
   at least one solid state light emitter coupled to said body for directing light into said channel; and
   at least one battery electrically connected to said at least one light emitter and coupled to said body, said at least one battery extending along at least one of said lingual side and said buccolabial side of said body.

2. The dental impression tray of claim 1 and including a housing that supports said at least one light emitter and said at least one battery.

3. The dental impression tray of claim 2, wherein said housing is detachably connected to said body.

4. The dental impression tray of claim 2, wherein said housing includes a chamber that receives and encloses said battery.

5. The dental impression tray of claim 4, wherein said housing includes a detachable handle section.

6. The dental impression tray of claim 5, wherein said housing includes a buccolabial section, wherein said chamber is located within said buccolabial section and wherein said handle is detachably connected to said buccolabial section.

7. The dental impression tray of claim 6, wherein said handle section sealingly engages said buccolabial section when said handle section and said buccolabial section are connected together.

8. The dental impression tray of claim 1, wherein said channel includes an upper channel section and a lower channel section.

9. The dental impression tray of claim 1 and including at least one flat substrate for supporting said at least one light emitter.

10. The dental impression tray of claim 1 and including a first substrate extending along said lingual side of said body and a second substrate distinct from said first substrate and extending along said buccolabial side of said body, and wherein said at least one solid state light emitter includes a number of light emitters mounted on said first substrate and a number of light emitters mounted on said second substrate.

11. The dental impression tray of claim 10, wherein said first substrate and said second substrate are detachably connected to said body.

12. The dental impression tray of claim 1, wherein said body includes a septum made of a series of optical fibers.

13. The dental impression tray of claim 1, wherein said housing is detachably connected to said body by a tongue and groove arrangement.

14. A dental impression tray comprising:
    a body having a channel for receiving a quantity of photocurable dental impression material, said body having a lingual side and a buccolabial side;
    a housing detachably connected to said body and extending along said lingual side and said buccolabial side of said body; and
    at least two arrays of solid state light emitters connected to said housing and including at least two distinct flat, emitter-supporting substrates, wherein at least one of said substrates extends along said lingual side of said body, and wherein at least one of said substrates extends along said buccolabial side of said body.

15. The dental impression tray of claim 14, wherein each of said substrates includes a printed circuit board.

16. The dental impression tray of claim 14, wherein each of said arrays includes a polymeric coating that transmits actinic radiation.

17. The dental impression tray of claim 14, wherein said channel is elongated, and wherein said housing is detachably connected to said body, said housing being detachable from said body by sliding said housing relative to said body in a direction along the longitudinal axis of the channel.

18. The dental impression of tray of claim 17, wherein said housing is connected to said body by a tongue and groove arrangement.

19. The dental impression tray of claim 14 and including at least one battery that extends along at least one of said lingual side and said buccolabial side, said at least one battery being supported by said housing.

20. The dental impression tray of claim 19, wherein said at least one battery is substantially enclosed by said housing.

21. A dental impression tray comprising:
    a body having an elongated channel for receiving a quantity of photocurable dental impression material, said body having a lingual side and a buccolabial side;
    a housing detachably connected to at least one of said lingual side and said buccolabial side of said body; and
    at least one solid state light emitter connected to said housing for directing light into said channel, wherein said housing is detachable from said body by sliding said housing relative to said body in a direction along the longitudinal axis of said channel.

22. The dental impression tray of claim 21, wherein said housing is detachably connected to said body by a tongue and groove arrangement.

23. The dental impression tray of claim 21 and including a battery that is connected to said housing and extends along said buccolabial side of said body.

24. The dental impression tray of claim 23, wherein said housing includes a detachable handle section.

25. The dental impression tray of claim 23, wherein said housing includes a chamber that receives said battery.

26. The dental impression tray of claim 21 and including at least one flat substrate for supporting said at least one solid state light emitter, wherein said at least one substrate extends along at least one of said lingual side and said buccolabial side of said body.

27. The dental impression tray of claim 21, wherein said body is made of a material that transmits actinic radiation.

* * * * *